US006691564B2

(12) United States Patent
Anderberg

(10) Patent No.: US 6,691,564 B2
(45) Date of Patent: Feb. 17, 2004

(54) HARDNESS TESTER

(75) Inventor: Eric Anderberg, Kirkland, IL (US)

(73) Assignee: Rams Rockford Products, Inc., Rockford, IL (US)

( * ) Notice: Subject to any disclaimer, the term of this patent is extended or adjusted under 35 U.S.C. 154(b) by 0 days.

(21) Appl. No.: 10/128,103

(22) Filed: Apr. 23, 2002

(65) Prior Publication Data

US 2003/0196480 A1 Oct. 23, 2003

(51) Int. Cl.[7] .................................................. G01N 3/42
(52) U.S. Cl. ...................................... 73/81; 73/82; 73/83
(58) Field of Search ....................................... 73/81–83

(56) References Cited

U.S. PATENT DOCUMENTS

| | | | |
|---|---|---|---|
| 3,590,630 A | * | 7/1971 | Ericksson ........................ 73/83 |
| 4,094,188 A | | 6/1978 | Bellouin et al. |
| 4,111,039 A | | 9/1978 | Yamawaki et al. |
| 4,116,047 A | * | 9/1978 | Hejkal ............................ 73/81 |
| 4,118,975 A | * | 10/1978 | Iwasaki ........................... 73/81 |
| 4,435,976 A | | 3/1984 | Edward, Jr. |
| 4,534,212 A | | 8/1985 | Targosz |
| 4,535,623 A | | 8/1985 | Gilberto |
| 4,667,509 A | | 5/1987 | Tobolski et al. |
| 4,671,104 A | | 6/1987 | Fischer |
| 4,773,258 A | | 9/1988 | Kiffe |
| 4,802,367 A | | 2/1989 | Petersen et al. |
| 4,820,051 A | | 4/1989 | Yanagisawa et al. |
| 5,062,293 A | | 11/1991 | Bakirov et al. |
| 5,067,346 A | | 11/1991 | Field |
| 5,305,633 A | | 4/1994 | Weissenbacher et al. |
| 5,433,215 A | | 7/1995 | Athanasiou et al. |
| 5,511,431 A | | 4/1996 | Hinton |
| 5,616,857 A | | 4/1997 | Merck, Jr. et al. |
| D394,015 S | | 5/1998 | Kellstedt, Jr. et al. |

OTHER PUBLICATIONS

United Tru–Blue II Hardness Tester Brochure, 4 pg., United Testing Systems, Flint, MI, No Date.
NewAge Hardness Tester Reference Catalog, 1989–90, 6 pg., Willow Grove, PA.
Clark Hardness Tester Brochure, 4 pg.; Sun–Tec Corp., Novi, MI, No Date.
Versitron Rockwell Hardness Testing System, Bulletin #820, 6 pg. NewAge Ind., PA, No Date.
Wilson Series 600 Rockwell Hardness Testers; 6 pg. Wilson Inst. Div. Canton, MA, No Date.
Standardization News, Nov. 1999; 2 pg.; Advertisement.
Rams Rockford Brochure, 4 pg., Rams Rockford Products, Rockford, Illinois, No Date.

* cited by examiner

Primary Examiner—Robert Raevis
(74) Attorney, Agent, or Firm—Leydig, Voit & Mayer, Ltd

(57) ABSTRACT

A hardness tester generally comprises a tester assembly is supported on a frame assembly. The tester assembly has a tester housing that supports a motor drivingly connected to a load cell and an indentor. The frame assembly includes a vertically oriented plate having a general C-shape defined by upper and lower arms connected by a main body. The plate is fabricated from a unitary sheet of metal to provide rigidity in the vertical direction. The tester assembly is selectively attachable to the frame assembly, and may be remotely employed as a stand-alone unit. A unique ball screw assembly is also provided for applying the testing load.

17 Claims, 5 Drawing Sheets

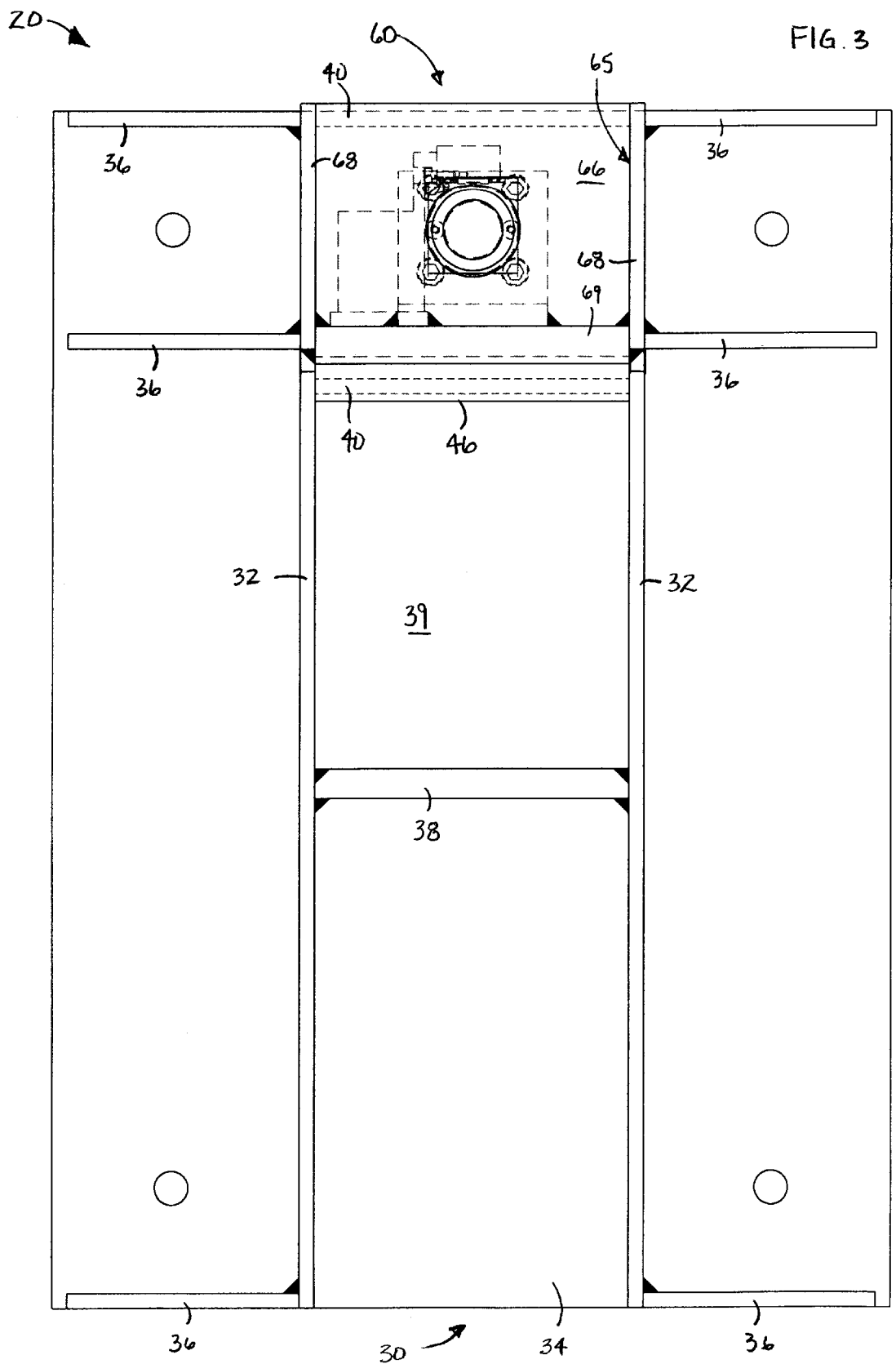

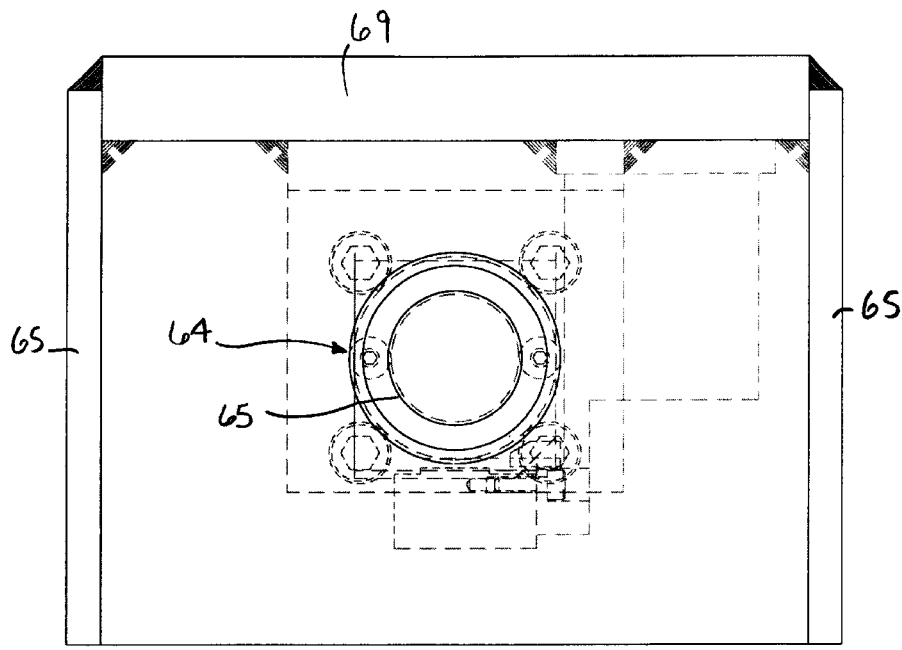
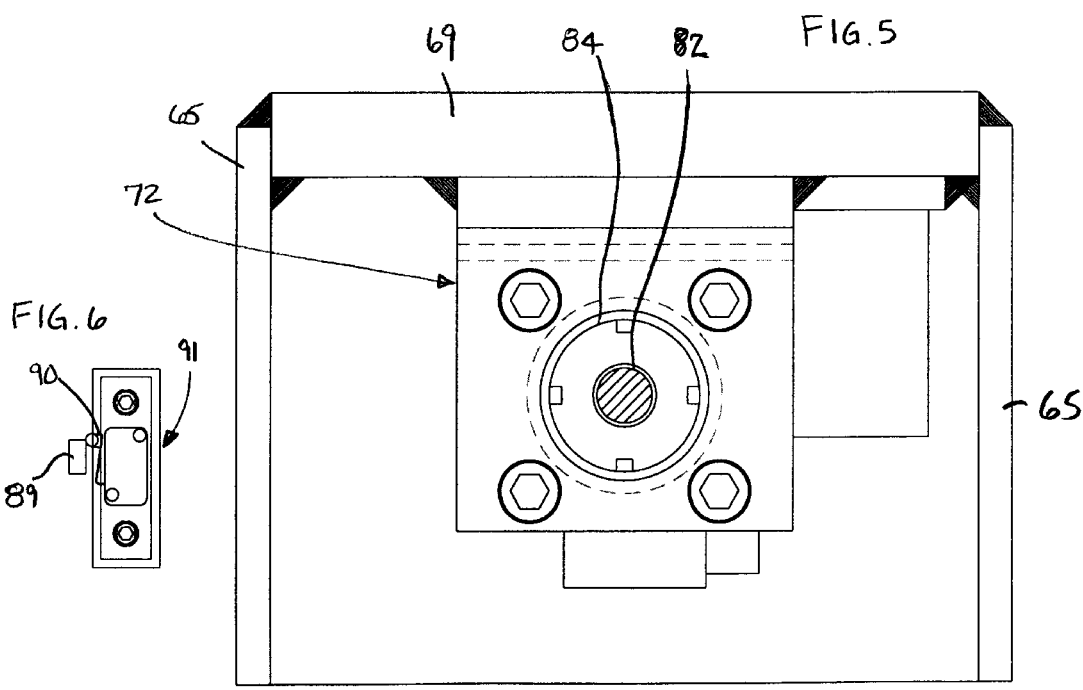

HARDNESS TESTER

FIELD OF THE INVENTION

This invention relates generally to equipment for testing material properties, and more specifically relates to hardness testers used to determine the hardness of a material.

BACKGROUND OF THE INVENTION

Penetration hardness testers are well-known in the art. These hardness testers generally include an indentor tip that is driven to apply a load to the test specimen. Some hardness testers known as deadweight testers utilize gravity acting on weights to create the force which drives the indentor into the test specimen. Other hardness testers utilize an electric motor to drive the indentor. In either case, the force or load on the indentor relative to the depth of penetration of the indentor into the surface of the specimen, or relative to the diameter of the indentation, will give a hardness number measured on a common scale such as Rockwell or Brinell.

Inaccuracies in testing arise due to many sources, such as relative movement between mechanical components. Recent improvements to such hardness testers have come by the use of various electronic equipment, such as load cells to measure the applied force and displacement sensors to measure the depth of penetration. Closed-loop systems utilizing a central processor or computer, especially in conjunction with load cells and displacement transducers, have provided improved reliability to hardness testers. Despite these advances, there remains a need to provide a hardness tester with improved accuracy.

Further, known hardness testers utilize a vertically adjustable anvil to properly position the test specimen at a discrete position for testing. However, not all specimens may easily be positioned on the anvil for testing. Hence, there exists a need to provide a hardness tester that is adaptable for different specimens, including for a variety of situations.

The invention provides a hardness tester which not only obtains improved accuracy, but also is adaptable to a variety of situations and specimens. These and other advantages of the invention, as well as additional inventive features, will be apparent from the description of the invention provided herein when taken in conjunction with the accompanying drawings.

BRIEF SUMMARY OF THE INVENTION

One embodiment of he present invention provides a hardness tester for determining the hardness of a specimen. The hardness tester generally comprises a tester assembly is supported on a frame assembly. The tester assembly has a tester housing that supports a motor drivingly connected to a load cell and an indentor. The frame assembly includes a vertically oriented plate having a general C-shape defined by upper and lower arms connected by a main body. The plate is fabricated from a unitary sheet of metal to provide rigidity in the vertical direction.

According to more detailed features of the embodiment, by virtue of the C-shaped plate, the upper and lower arms deflect less than 0.0015 inches apart in response to a separating force of 330 lbs. The lower arm supports an anvil for supporting the specimen. It is also preferable to provide a second vertically oriented plate having a general C-shape, the second plate being laterally spaced from the first plate to define side walls of the frame. Here, the free ends of the upper arms are connected by a mounting plate having a mounting surface engaging the tester housing.

In another embodiment of the present invention, a hardness tester is provided that generally comprises a frame assembly and a tester assembly. The frame assembly includes an upper arm and a lower arm, and the tester assembly includes a tester housing supporting a motor drivingly connected to a load cell and an indentor. The tester assembly is selectively attachable to the frame assembly at a frame mounting surface defined by the upper arm of the frame assembly.

According to more detailed features of this embodiment, the tester assembly includes a tester mounting surface for engaging the frame mounting surface. Preferably, the tester mounting surface and frame mounting surface are keyed together. It is also preferable that the tester mounting surface and the frame mounting surface extend at least 4 inches in the vertical direction. The tester mounting surface and frame mounting surface each include a plurality of corresponding mounting holes for selectively attaching the tester and frame assemblies, typically by threaded fasteners.

In yet another embodiment of the present invention, a hardness tester is provided that generally comprises a tester housing supporting a motor operatively connected to a ball screw assembly. The ball screw assembly is connected to the tester housing and includes a ball screw, a ball spline, and a ball spline bearing. The ball screw is operatively connected to the motor. The ball spline has a hollow center for receiving the ball screw, and includes a ball nut securely attached thereto. A downward end of the ball spline is directly connected to a load cell and an indentor. The ball spline bearing is attached to the housing and receives the ball spline to prevent rotation of the ball spline. The ball nut threadingly engages the ball screw for transforming the rotational movement of the ball screw into linear movement of the ball spline and indentor.

According to more detailed aspects of this embodiment, the ball spline includes a plurality of circumferentially spaced grooves extending along the length of the ball spline, the spine bearing engaging each groove to prevent rotation of the ball spline and guide linear movement. Preferably, a displacement sensor is provided that has a read head and a tape scale; the tape scale being attached to the outer periphery of the ball spline and the read head being attached to the tester housing and positioned to read the tape scale. A CPU is operatively connected to the motor, displacement sensor, and load cell to control the movement of the ball spline and indentor to perform hardness tests. Preferably, first and second limit switches are connected to the tester housing, the first and second limit switches being vertically spaced to define an operating range for the ball spline and indentor.

BRIEF DESCRIPTION OF THE DRAWINGS

FIG. 3 is a partially cut-away top view of the hardness tester of FIG. 1;

FIG. 4 is a cross-sectional view, taken about the line 4—4 in FIG. 2;

FIG. 5 is a cross-sectional view, taken about the line 5—5 in FIG. 2;

FIG. 6 is a cross-sectional view, taken about the line 6—6 in FIG. 2;

DETAILED DESCRIPTION OF THE INVENTION

Figure 1:
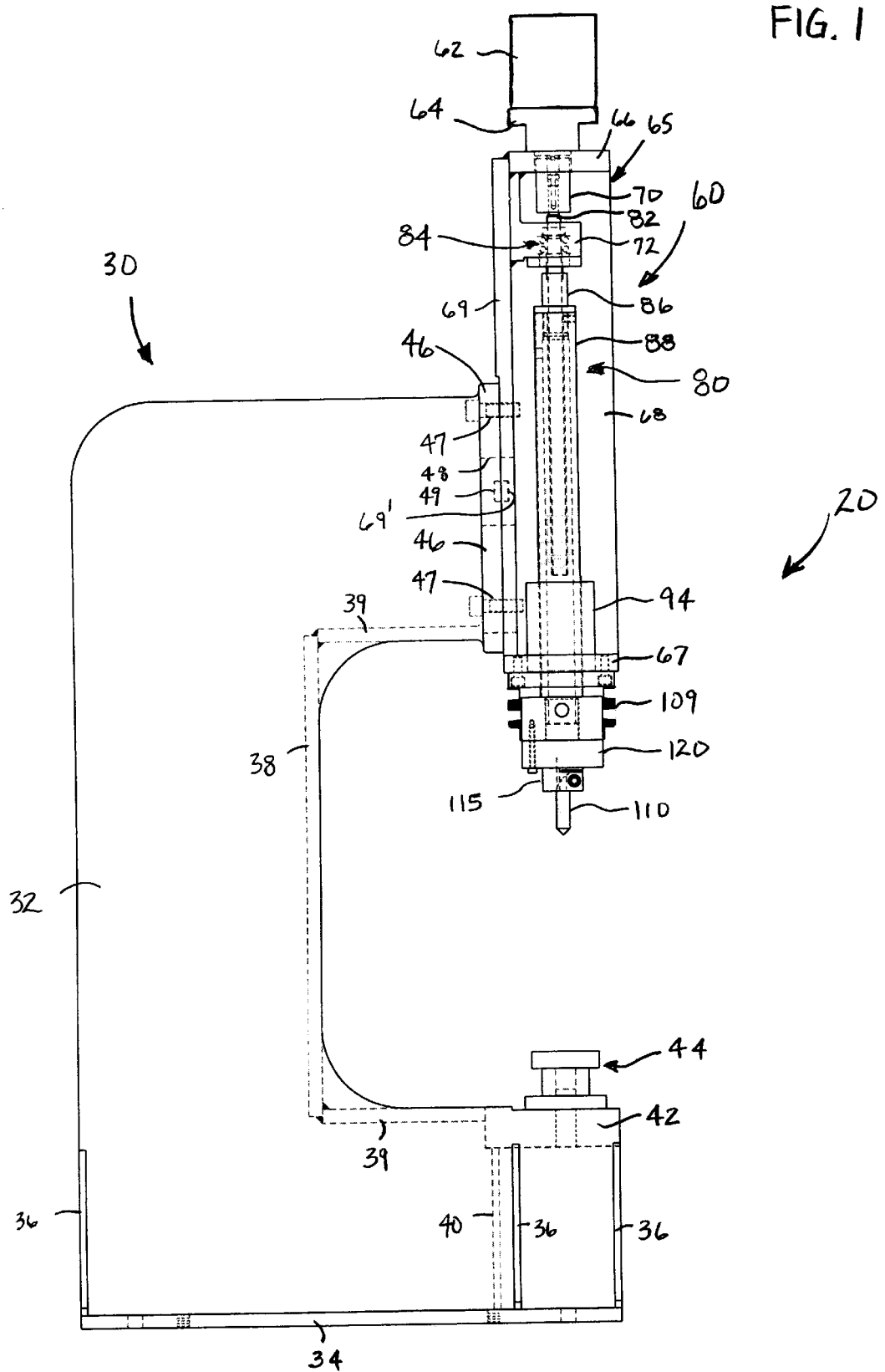
FIG. 1 is a partially cut-away side view of an embodiment of the hardness tester constructed in accordance with the teachings of the present invention.

Turning now to the figures, the hardness tester 20 generally comprises a frame assembly 30 connected to a tester assembly 60. The frame assembly 30 is best seen with reference to FIGS. 1–3, and generally comprises a very rigid housing including two fabricated sidewalls 32 of a general C-shape. The sidewalls 32 are connected to a bottom wall 34, while six triangular supports 36 provide lateral support to the sidewalls 32. Four holes in the bottom wall 34 can be used to securely mount and level the frame assembly 30. The inner edge of the C-shaped sidewalls 32 are supported by a vertical plate 38 and two horizontal plates 39 extending between the sidewalls.

Adjacent the end of the lower arm of the C-shape frame 30 are two support plates 40 upon which a block 42 rests. The block 42 supports an anvil 44, which in turn supports the test specimen. At the end of the upper arm of the C-shape frame 30 is a vertically oriented mounting plate 46. The mounting plate 46 includes four mounting holes 47 for bolting the tester assembly 60 to the frame assembly 30. The mounting plate 46 also includes a large hole 48 for passing wires and the like from the tester assembly 60, since the frame 30 can be used to house various electronic components of the tester 20 such as the central processing unit (CPU), the power supply, the signal conditioner, and the capacitor to name a few. Finally, the mounting plate 46 includes two laterally spaced key members 49 that project forwardly to assist in mounting the tester assembly 60, as will be described in more detail herein.

The frame assembly 30 is preferably welded together as shown, and a housing or cover (not shown) encloses the frame members. Importantly, the sidewalls 32 are fabricated from a single sheet of material such as sheet steel of at least ⅜" thickness. Alternately, the frame could be cast iron. By fabricating the frame in this manner, the cost and difficulty of casting the frame is eliminated, while a stronger frame is provided. More specifically, the fabricated C-shape reduces the deflection between the upper arm of the C-shape and the lower arm of the C-shape during testing.

It will be recognized that the tester assembly 60 applies a downward force on the specimen supported on the anvil 44, and hence lower arm of the frame. This downward force thus attempts to separate the upper and lower arms of the frame, and they in fact do separate. This separation can be incorrectly attributed to penetration of the specimen, and computer calibration or control cannot completely eliminate this error. As an example, the major load on a Rockwell test is typically 60 kg, 100 kg or 150 kg (330 lbs.), while one Rockwell Hardness Number is equal to about 0.00008 inches of penetration. While the frames of some hardness testers have been measured to separate or deflect 0.005 inches or more at 150 kg, the frame 30 of the present invention deflects less than 0.0015 inches at 150 kg.

Turning now to the tester assembly 60, the assembly generally includes an electric servomotor 62 driving a ball screw assembly 80, which in turn is attached to an indentor 110 and load cell 120 for applying a measured load to the specimen. More specifically, the tester assembly 60 generally includes a tester housing 65 comprising a top plate 66, a bottom plate 67, two opposing side plates 68, and a mounting plate 69. The mounting plate 69, and hence the tester housing 65 and assembly 60 are securely attached to the upper arm of the C-shaped frame via the mounting plate 46. A cover (not shown) encloses the tester housing 65 to keep the components free from dirt and dust or other impediments.

The tester mounting plate 69 includes keyways 69' sized and positioned to correspond with key members 49 of the frame mounting plate 46. By keying the tester mounting plate 69 to the frame mounting plate 46, the tester assembly 60 may be easily and quickly positioned on the frame assembly 30 for attachment via mounting holes 47 that mate with mounting holes on the tester mounting plate 69. Bolts are used to rigidly attach the mounting plates 49, 69, which interface over a long vertical surface, ensuring a rigid mount and transfer of force from the tester housing 65 to the frame assembly 30. In the illustrated embodiment, the mounting plates 49, 69 mate over a surface that is about 11" tall and about 5" wide, although other sized mating surfaces may be utilized.

It will also be recognized that by allowing the tester assembly 60 to be selectively attachable to the frame assembly 30, the tester assembly may be separately employed without the frame. Some particular applications or specimens cannot be brought to the hardness tester, or may not fit within a particular frame. For example, the hardness of large metal gears is ideally tested, but their large size and shape prevent testing on existing hardness testers. With the present invention, the tester assembly 60 may be directly applied to such gears, typically by way of a mounting plate structured similarly to that of frame mounting plate 46, which then can be attached by any convenient manner to the gear. For example, the similar mounting plate may be provided with addition mounting holes to mount the plate to the gear, or another structure fixed to the gear. Hence other fixtures may be developed for any particular mounting situation. It will also be recognized that the tester assembly 60 may simply be attached to a different frame assembly of alternate sizes or shapes. Many remote applications are possible with the selectively attachable tester assembly as will be readily recognized by those skilled in the art.

The upper end of the tester housing 65 supports the servomotor 62 in a position above the tester housing. The servomotor includes an encoder, the motor and encoder combination being purchased as a single unit, such as the Kollmorgan Servomotor with encoder. The encoder monitors the rotation of a driveshaft within the servomotor itself and can be used for various control applications as will be described in more detail herein. The output of the servomotor is operatively connected to a planetary gear reducer 64, the output shaft 65 (FIG. 4) of which is operatively connected to the ball screw 82 of the ball screw assembly 80 by way of a coupler 70.

The ball screw assembly 80 includes a driving screw 82, the upper end of which is held within the housing by a double row angle contact bearing 84 suitably connected to the housing by support plates 72 (see also FIG. 5). The driving screw 82 operatively engages a ball nut 86 to translate the rotational movement of the screw into linear movement of the ball nut 86, and ultimately the indentor 110. The ball nut 86 is attached to the upper end of a ball spline 88, and preferably the ball nut 86 and ball spline 88 are threadingly engaged.

Figure 2:
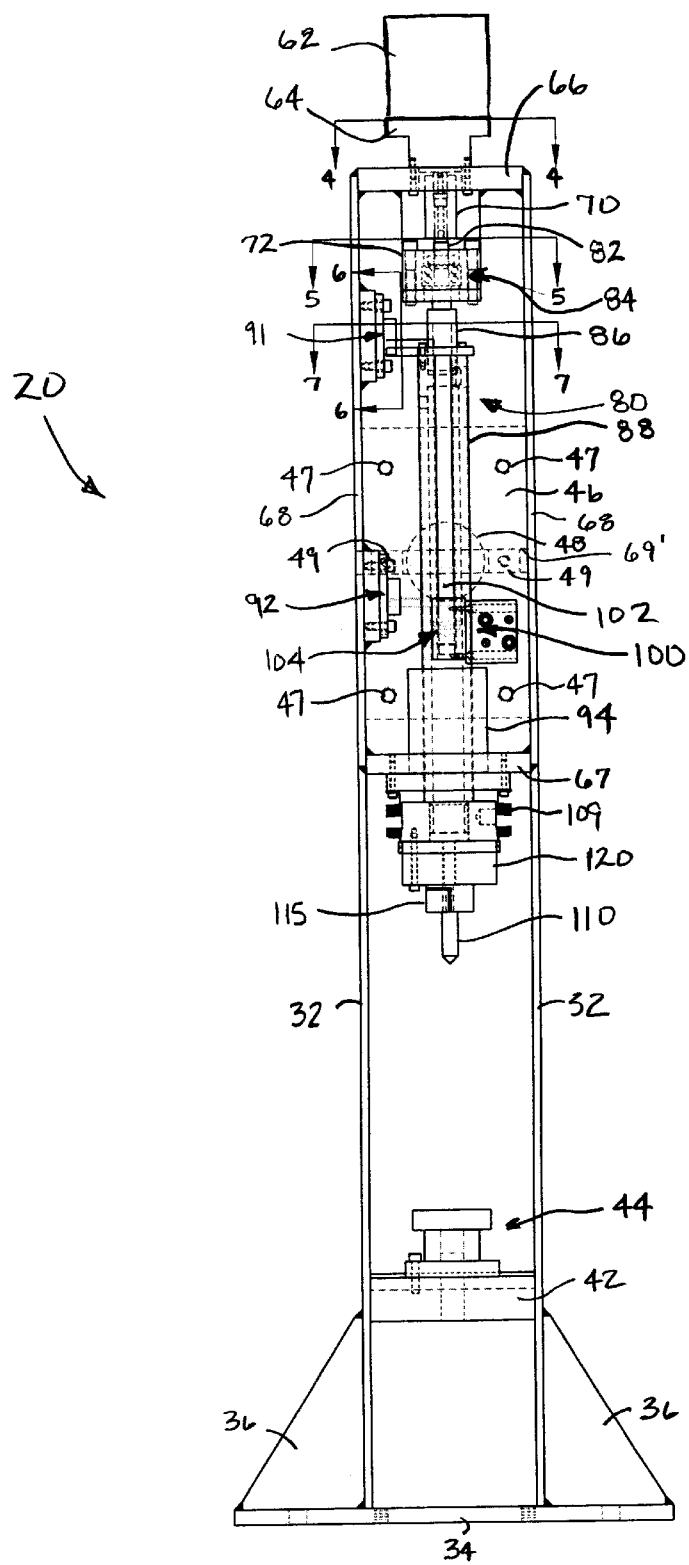
FIG. 2 is a partially cut-away front view of the hardness tester of FIG. 1.
Figure 7:
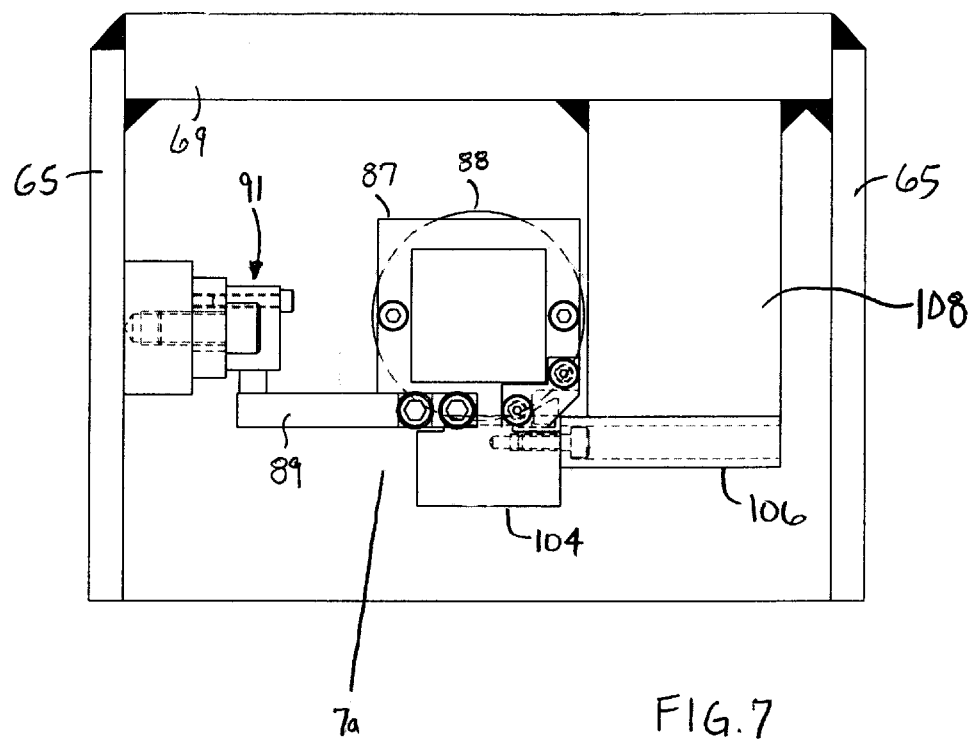
FIG. 7 is a cross-sectional view, taken about the line 7—7 in FIG. 2.
Figure 7A:
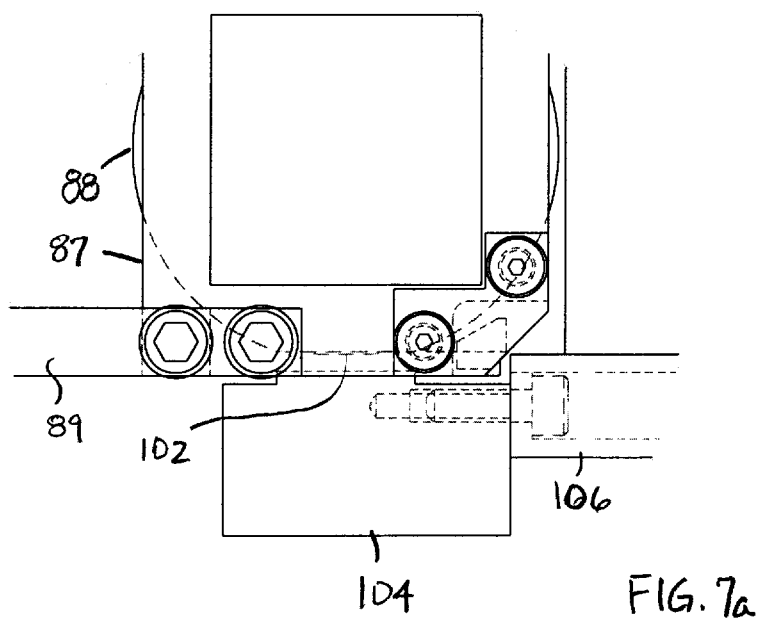
FIG. 7a is an enlarged view, partially cut-away, taken about the circle 7a in FIG. 7.

A plate 87 is attached to the upper surface of the ball spline 88, preferably between the ball nut 86 and spline 88, and has a trigger arm 89 extending laterally therefrom (FIGS. 7 and 7a). As best seen in FIGS. 2 and 6, the tester assembly 60 includes an upper limit switch 91 and a lower limit switch 92, each having a limit arm 90 that is contacted by the trigger arm 89 as it passes by one of the switches 91, 92. The limit switches 91, 92 are attached to the tester housing 65 at upper and lower ends to define the extents of the operating range (travel) for the tester, the triggering of which causes the controller to stop the motor 62 and hence vertical movement of the ball spline 88 and indentor 110.

Returning to the ball screw assembly 80, the ball nut 84 is attached to the ball spline 88 and operatively engaged (via threads) to ball screw 82. The lower end of the ball spline 88 is held against rotation by a ball spline bearing 94. More specifically, the ball spline includes three outwardly opening and vertically extending grooves which receive spring loaded ball bearings of the ball spline bearing 94. Accordingly, as the screw 82 is rotated, the ball spline 88 moves upwardly or downwardly via the threaded connection with the nut 84.

With reference to FIGS. 2, 7 and 7a, a position or displacement sensor 100, which includes a tape scale 102 and read head 104, is employed in the tester assembly 60. The ball spline 88 is generally circular, but includes a flat strip ground on its outer surface, the flat strip extending vertically along its length. The tape scale 102 (FIGS. 2 and 7a) attached to the strip, preferably by an adhesive. The read head 104 is suitably mounted to the tester housing 65, preferably by an attachment plate 106 attached to a block 108 welded to the mounting plate 69 of the tester assembly 60 (FIG. 7). The read head 104 is positioned to read the tape scale 102 and produce output signals corresponding to the position of the tape scale 102, and hence the ball spline 88. In one embodiment, the displacement sensor may comprise a Renishaw Read Head #RGH22Z30F00A, Mark Actuator #RGM22S, and Micron Pitch Tape Scale #RGS-S-20.

The ball spline 88 extends through the lower end of the spline bearing 94 and the tester housing 65, and is directly connected to a load cell 120. An accordion-type cover 109 may be attached to the load cell 120 and a bottom of the tester assembly 60 and housing 65 to keep the tester components clean and free of debris. The load cell 120 is in turn connected to an adapter 115, which is designed to receive various types of indenters 110.

Operation of the hardness tester 20 occurs, in part, through a closed-loop feedback system which will be described with reference to a Rockwell Hardness test, although it will be recognized that other hardness or penetration tests may be employed by the present invention. The system generally includes the CPU and user interface, the servomotor and encoder, the ball screw assembly, the load cell, and the displacement sensor. During operation, the specimen is placed on the anvil and the test is initiated via the user interface. The indentor begins at a default position. The CPU sends a signal to the servomotor to rotate the ball screw, driving the ball spline, load cell, and indentor downwardly until the indentor reaches the material. This portion of the test does not rely on the displacement sensor or on the servo motor encoder, and thus is "open-loop", although the feedback from the load cell is monitored to determine when the indentor first touches the specimen.

At this point, the control switches to closed loop operation. The position of the indentor is monitored via the displacement sensor, while the readings from the load cell are used to place a first minor load on the material. The CPU will recognize from the load cell output when the minor load is reached and will hold that minor load for a fixed period of time, noting the position of the indentor. Next, the CPU will cause the servomotor to drive the ball spline, load cell, and indentor to induce a larger, major load. The CPU will recognize when this load has been reached by the output received from the load cell and will hold the major load for a fixed amount of time, again noting the position of the indentor via the displacement sensor. Then, the CPU will instruct the servomotor to raise the ball spline, load cell, and indentor until the minor load is again applied to the material being tested. The CPU will again record the position of the indentor when the minor load is applied for the second time, and then the displacement sensor will end its monitoring duties.

The CPU will then instruct the servomotor to raise the ball spline, load cell, and indentor to the default position. This movement is controlled by the CPU via feedback from the encoder in the servomotor. Generally, the encoder operates on a much coarser scale than the displacement sensor, and is not capable of conducting the hardness tests at the required precision and accuracy. However, the use of the encoder during non-load movement allows the ball spline, load cell, and indentor to be returned to its position very quickly. Further, the encoder is rotary based and monitors the rotation of the shaft of the motor which is translated into a linear displacement, but does not directly monitor the linear movement. Alternately, the motor is driven in an open-loop system to move the ball spline and indentor upwardly, relying on the upper limit switch to be triggered and stop the ball spline and indentor in the default position. The CPU, based on the particular minor and major loads applied and the positions sensed at each of these three load conditions, can compute the hardness of the specimen according to a standard hardness scale such as Rockwell or Brinell.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hardness tester for determining the hardness of a specimen, the hardness tester comprising:

a frame assembly;

a tester assembly supported on the frame assembly and having a tester housing that supports a motor drivingly connected to a load cell and an indentor;

the frame assembly including a vertically oriented plate having a general C-shape defined by upper and lower arms connected by a main body, the plate being fabricated from a unitary sheet of metal to provide rigidity in the vertical direction.

2. The hardness tester of claim 1, wherein the upper and lower arms deflect less than 0.0015 inches apart in response to a separating force of 330 lbs.

3. The hardness tester of claim 1, wherein the tester assembly is connected to the frame assembly at a free end of the upper arm of the vertical plate.

4. The hardness tester of claim 3, wherein the tester assembly contacts the frame assembly over a vertical surface extending at least 4 inches.

5. The hardness tester of claim 1, wherein the lower arm supports an anvil for supporting the specimen.

6. The hardness tester of claim 1, further comprising a second vertically oriented plate having a general C-shape, the second plate being laterally spaced from the first plate to define side walls of the frame.

7. The hardness tester of claim 6, wherein free ends of the upper arms are connected by a mounting plate having a mounting surface engaging the tester housing.

8. The hardness tester of claim 7, wherein the mounting surface has a vertical height of at least 4 inches.

9. The hardness tester of claim 7, wherein the tester housing is keyed to the mounting plate for proper alignment.

10. The hardness tester of claim 1, wherein the tester assembly is selectively attachable to the frame assembly.

11. A hardness tester comprising:

a frame assembly having an upper arm and a lower arm;

a tester assembly selectively attachable to the frame assembly and having a tester housing supporting a motor drivingly connected to a load cell and an indentor;

the upper arm of the frame assembly defining a frame mounting surface for directly engaging tester assembly when attached thereto;

wherein the tester assembly includes a tester mounting surface for engaging the frame mounting surface; and wherein the tester mounting surface and frame mounting surface are keyed together.

12. The hardness tester of claim 11, wherein the frame mounting surface includes a projecting key member and the tester mounting surface includes a keyway structured to receive the key member.

13. The hardness tester of claim 11, wherein the tester assembly is selectively attachable to the frame assembly by threaded fasteners.

14. The hardness tester of claim 11, wherein the tester mounting surface and frame mounting surface each include a plurality of corresponding mounting holes for selectively attaching the tester and frame assemblies.

15. The hardness tester of claim 11, wherein the tester and frame mounting surfaces are planar.

16. The hardness tester of claim 11, wherein the tester and frame mounting surfaces span at least 3 square inches.

17. A hardness tester comprising:

a frame assembly having an upper arm and a lower arm;

a tester assembly selectively attachable to the frame assembly and having a tester housing,supporting a motor drivingly connected to a load cell and an indentor;

the upper arm of the frame assembly defining a frame mounting surface for directly engaging tester assembly when attached thereto;

wherein the tester assembly includes a tester mounting surface for engaging the frame mounting surface; and wherein the tester mounting surface and frame mounting surface extend at least 4 inches in the vertical direction.

* * * * *

UNITED STATES PATENT AND TRADEMARK OFFICE
CERTIFICATE OF CORRECTION

PATENT NO. : 6,691,564 B2
DATED : February 17, 2004
INVENTOR(S) : Eric Anderberg It is certified that error appears in the above-identified patent and that said Letters Patent is hereby corrected as shown below:

<u>Column 8,</u>
Line 32, after "tester housing" delete "," and replace with a space.

Signed and Sealed this

Fifteenth Day of June, 2004

JON W. DUDAS
*Acting Director of the United States Patent and Trademark Office*